United States Patent
Silen

(10) Patent No.: US 9,901,607 B2
(45) Date of Patent: Feb. 27, 2018

(54) SMOKELESS CANNABIS COMPOSITION AND METHOD OF MANUFACTURE

(71) Applicant: Mark J. Silen, Pueblo, CO (US)

(72) Inventor: Mark J. Silen, Pueblo, CO (US)

(*) Notice: Subject to any disclaimer, the term of this patent is extended or adjusted under 35 U.S.C. 154(b) by 0 days.

(21) Appl. No.: 15/219,051

(22) Filed: Jul. 25, 2016

(65) Prior Publication Data

US 2017/0312326 A1 Nov. 2, 2017

Related U.S. Application Data

(60) Provisional application No. 62/329,019, filed on Apr. 28, 2016.

(51) Int. Cl.

| | |
|---|---|
| *A61K 36/185* | (2006.01) |
| *A61K 9/08* | (2006.01) |
| *A61K 9/00* | (2006.01) |
| *A61K 35/644* | (2015.01) |
| *A61K 47/46* | (2006.01) |
| *A61K 31/352* | (2006.01) |
| *A61K 47/10* | (2017.01) |
| *A61K 36/064* | (2006.01) |

(52) U.S. Cl.
CPC .......... *A61K 36/185* (2013.01); *A61K 9/0053* (2013.01); *A61K 9/0056* (2013.01); *A61K 9/08* (2013.01); *A61K 31/352* (2013.01); *A61K 35/644* (2013.01); *A61K 36/064* (2013.01); *A61K 47/10* (2013.01); *A61K 47/46* (2013.01); *A61K 2236/10* (2013.01); *A61K 2236/11* (2013.01); *A61K 2236/13* (2013.01); *A61K 2236/15* (2013.01); *A61K 2236/17* (2013.01); *A61K 2236/19* (2013.01); *A61K 2236/33* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | |
|---|---|---|
| 4,127,136 A | 11/1978 | Comber |
| 6,584,980 B1 | 7/2003 | Russo |
| 7,810,507 B2 | 10/2010 | Dube et al. |
| 8,784,872 B2 | 7/2014 | Oronsky et al. |
| 8,910,630 B2 | 12/2014 | Todd |
| 2004/0049059 A1 | 3/2004 | Mueller |
| 2004/0192760 A1* | 9/2004 | Whittle ............... A61K 9/0031 514/454 |
| 2006/0240156 A1* | 10/2006 | Panarisi ................ A23L 27/30 426/120 |
| 2010/0187143 A1* | 7/2010 | Essen .................... A24B 15/16 206/260 |
| 2011/0038915 A1 | 2/2011 | Gonzalez |
| 2011/0097283 A1 | 4/2011 | Damme et al. |
| 2014/0166028 A1 | 6/2014 | Fuisz et al. |
| 2014/0209109 A1 | 7/2014 | Larson |
| 2016/0199299 A1 | 7/2016 | Uren |

OTHER PUBLICATIONS

Ethyl alcohol, MSDS, 2014, 13 pages.*

* cited by examiner

*Primary Examiner* — Kyle Purdy
(74) *Attorney, Agent, or Firm* — IDP Patent Services; Olav M. Underdal

(57) ABSTRACT

A *cannabis* composition includes a *cannabis* material and an additive solution. *Cannabis* material includes flowers, sugar leaves, and fan leaves from a *cannabis* plant, and can be configured to be finely cut or coarsely cut. An additive solution includes honey and a *cannabis* extract. Further disclosed is a method of manufacture of a *cannabis* composition, including a method for allowing a *cannabis* composition to ferment and a method of heating a *cannabis* composition.

30 Claims, 2 Drawing Sheets

Method of manufacture of a cannabis composition

Scored Cannabis Stick

SMOKELESS CANNABIS COMPOSITION AND METHOD OF MANUFACTURE

CROSS-REFERENCE TO RELATED APPLICATIONS

This application claims the benefit of U.S. Provisional Application No. 62/329,019, filed Apr. 28, 2016.

FIELD OF THE INVENTION

The present invention relates generally to the field of *cannabis* compositions for medicinal and recreational use, and more particularly to compositions and methods of manufacture of smokeless *cannabis*.

BACKGROUND OF THE INVENTION

*Cannabis* has been used for thousands of years as a source for hemp fiber and hemp oils, as well as for medicinal and recreational purposes. The tetrahydrocannabinol (THC) found in *cannabis*, along with numerous of other cannabinoids, can be used to treat a variety of ailments, such as nausea, pain, and neurological problems, in addition to causing psychoactive effects. Modern day patients or recreational users often consume *cannabis* by smoking or vaporizing the dried flower buds and subtending leaves, also known as marijuana, or by ingesting food made with *cannabis* extracts, such as hash oil.

There are numerous shortcomings to current *cannabis* usage methods. Smoking marijuana can cause inflammation of the lungs and reduce lung capacity. Vaporizing can involve expensive, battery powered devices, such as e-cigarettes, that often require recharging and repair. Eating food made with *cannabis* extracts leads to problems in judging the time necessary for any psychoactive effects to take place, as there are many variables involved, including the user's metabolism and the contents of the stomach at the time of ingestion. In some cases, the psychoactive effects of ingested *cannabis* can be delayed by up to two hours and may last for hours afterward, making it difficult to correctly estimate the desired amount of *cannabis* to consume.

As such, considering the foregoing, it may be appreciated that there continues to be a need for novel and improved compositions and methods for consuming *cannabis* that is not harmful to the lungs, does not require a separate piece of equipment to function, and can easily be discarded during usage.

SUMMARY OF THE INVENTION

The foregoing needs are met, to a great extent, by the present invention, wherein in aspects of this invention, enhancements are provided to the existing model of *cannabis* compositions and methods of manufacture of *cannabis* compositions.

In an aspect, a *cannabis* composition adapted for oral use, can include:
  a) a *cannabis* material; and
  b) an additive solution.

In related aspects, the *cannabis* material can include flowers, sugar leaves, and fan leaves from *cannabis* plants. The *cannabis* material can further include finely cut *cannabis* material which has an average particle size in a range of approximately 0.3 mm to 2 mm, and coarsely cut *cannabis* material which has an average particle size greater than approximately 2 mm.

In related aspects, the additive solution can include honey and a *cannabis* extract, which can be configured as a *cannabis* extract oil.

In related aspects, the additive solution can include grain alcohol.

In an aspect, a method of manufacture of a *cannabis* composition adapted for oral use, can include:
  a) providing a *cannabis* material;
  b) adding an additive solution to the *cannabis* material, thereby creating a *cannabis* composition;
  c) allowing the *cannabis* composition to ferment for a first period of time;
  d) heating the *cannabis* material at a first temperature for a second period of time.

In related aspects, the first period of time can be in a range of approximately 12 to 36 hours.

In related aspects, the first temperature can be in a range of approximately 150° F. to 250° F.

In related aspects, the second period of time can be in a range of approximately 15 to 90 minutes.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
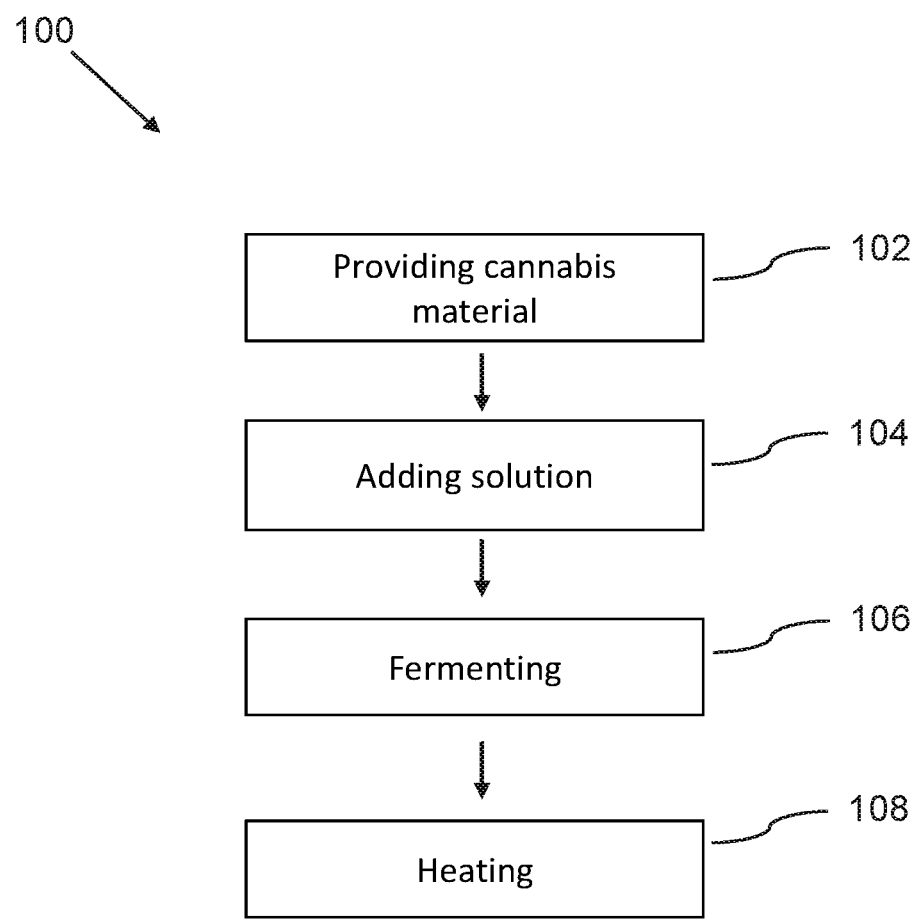
FIG. 1 is a schematic diagram illustrating a method of manufacture of a *cannabis* composition, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In a related embodiment, a *cannabis* composition can be adapted for oral use, such that the *cannabis* composition can be referred to as smokeless *cannabis*. Smokeless *cannabis* allows for the controlled release of cannabinoids, such as THC and cannabidiol (CBD), found in *cannabis*, thereby providing prolonged psychoactive and/or medicinal effects. Similar to smokeless tobacco products, smokeless *cannabis* can take the form of a chew, a dip, or a stick that can be placed in a user's mouth, such that the active components of the *cannabis* mix with saliva and are absorbed into the bloodstream through the mouth tissues.

In a related embodiment, *Cannabis* is a genus of flowering plant that includes three species or subspecies: *sativa*, *indica*, and *ruderalis*. *Cannabis* is often referred to generally as *cannabis*. When referred to hereinafter, a *cannabis* plant is defined as a plant included in the *Cannabis* genus, and *cannabis* material is defined as plant material derived from *Cannabis*.

In an embodiment, a *cannabis* composition adapted for oral use, can include:
a) a *cannabis* material; and
b) an additive solution.

In a related embodiment, the *cannabis* material can include material from the cola, also known as the terminal bud, of *cannabis* plants. Colas can include the calyxes, or the flowers, as well as the small leaves subtending the flowers, commonly referred to as sugar leaves. The flowers and leaves are often referred to generally as marijuana. While flowers usually comprise the major source of THC in colas, sugar leaves can also comprise small amounts of THC.

In a related embodiment, the *cannabis* material can include material from the fan leaves, which are the large leaves extending from the stems of *cannabis* plants. Fan leaves are known to comprise small amounts of THC.

In a related embodiment, the *cannabis* material can comprise finely cut *cannabis* material. Finely cut *cannabis* material can include material that has been ground, shredded, sifted, or otherwise broken up into components having an average particle size in the range of approximately 0.3 mm to 2 mm, wherein average particle size is determined as a diameter of a volume equivalent sphere.

In a related embodiment, the *cannabis* material can comprise coarsely cut *cannabis* material. Coarsely cut *cannabis* material can include material that has been ground, shredded, sifted, or otherwise broken up into components having an average particle size greater than 2 mm, wherein average particle size is determined as a diameter of a volume equivalent sphere.

In a related embodiment, the *cannabis* material can be made from *cannabis* plant that has been grown using a fertilizer comprising brewer's yeast, more specifically referred to as *Saccharomyces cerevisiae*.

In a related embodiment, the additive solution can comprise rectified alcohol, which is a highly concentrated ethanol, which has been purified by repeated distillation, and is commonly known as grain alcohol. For example, the additive solution can comprise grain alcohol with a concentration in a range of approximately 90 to 98 percent alcohol by volume.

In a related embodiment, the additive solution can comprise a concentrate derived from *cannabis*. The concentrate can be configured as a *cannabis* extract, such as a *cannabis* extract oil. *Cannabis* extract oil can have a wide variety of manufacturing processes and ingredients. Certain *cannabis* extract oils can be made by extracting oil from *cannabis* material using a solvent, such as grain alcohol. *Cannabis* extract oils can have a variety of different properties. In one embodiment, a *cannabis* extract oil can have THC levels in the range of approximately 15-70%.

In a related embodiment, the *cannabis* extract oil can be manufactured from *cannabis* material including flower material, sugar leaf material, fan leaf material, or a combination thereof. In certain embodiments, the *cannabis* extract oil can be manufactured from a whole *cannabis* plant, such that the oil is simultaneously extracted from the stem of the plant in addition to the flowers, sugar leaves, and fan leaves.

In a related embodiment, a *cannabis* extract oil commonly known as Rick Simpson Oil™ (RSO) can be produced by combining 750 ml of grain alcohol with 168 g (6 oz.) of a whole *cannabis* plant and mixing for 5 to 10 minutes. The mixture is then strained or sifted through a fine mesh into a vessel and heated at approximately 65° C. to 95° C. until the alcohol evaporates. The resultant is approximately 10 to 20 g of RSO, which has been used as a topical treatment for a wide variety of ailments.

In a related embodiment, the additive solution can comprise honey. The honey can be configured to enhance the flavor of the *cannabis* composition during oral use, in addition to honey's preservative, antibacterial, and bacteriostatic properties. The honey can also be configured such that it acts to bind the *cannabis* material together in order to improve the texture and consistency of the *cannabis* composition during oral use.

In a related embodiment, the additive solution can comprise honey and a *cannabis* extract oil, wherein the *cannabis* material can comprise at least approximately 70% of the total dry weight of the *cannabis* composition. In certain embodiments, the *cannabis* extract oil can comprise at least approximately 1% of the total dry weight of the *cannabis* composition, and the honey can comprise at least approximately 15% of the total dry weight of the *cannabis* composition.

In a related embodiment, the additive solution can comprise a mixture of grain alcohol, honey, and *cannabis* extract oil. The grain alcohol can be used to dilute the honey and *cannabis* extract oil such that the honey and *cannabis* extract oil can be easily combined with the *cannabis* material, such as by spraying the additive solution onto the *cannabis* material. The additive solution can be configured such that the grain alcohol substantially evaporates shortly after the additive solution is combined with the *cannabis* material, such that the amount of grain alcohol does not factor into the dry weight of the *cannabis* composition.

In a related embodiment, the additive solution can comprise approximately one part *cannabis* extract oil, one part honey, and three parts grain alcohol, by volume.

In a related embodiment, the additive solution can comprise approximately 30% honey, approximately 2% *cannabis* extract oil, and approximately 68% grain alcohol, by weight. In certain embodiments, the weight ratio of honey to *cannabis* extract oil can be about 10:1 to about 20:1.

In a related embodiment, the additive solution can further include brewer's yeast, for example in range of 0.25-2 grams of brewer's yeast per liter of the additive solution.

In a related embodiment, the *cannabis* composition can comprise about 0.5 gram of *cannabis* extract oil per ounce of *cannabis* material, or a range of 0.25 gram to 1 gram of *cannabis* extract oil per ounce of *cannabis* material.

In a related embodiment, the *cannabis* composition can comprise about 5 ml of honey per ounce of *cannabis* material, or a range of 2.5 to 10 ml of honey per ounce of *cannabis* material.

In a related embodiment, the additive solution can comprise a first additive solution and a second additive solution. The first additive solution can comprise a *cannabis* extract oil and grain alcohol. In certain embodiments, the first additive solution can comprise approximately 4% *cannabis* extract and approximately 96% grain alcohol, by weight.

In a related embodiment, the second additive solution can comprise honey and grain alcohol. In certain embodiments, the second additive solution can comprise approximately 64% honey and approximately 36% grain alcohol, by weight.

In a related embodiment, the *cannabis* composition can be configured in a variety of different well-known forms, such as a dip, chew, or stick (also known as a plug or brick). In one embodiment, a *cannabis* composition configured as a dip can include *cannabis* material comprising finely cut flower material, and an additive solution comprising grain alcohol, a *cannabis* extract oil, and honey.

In a related embodiment, a *cannabis* composition configured as a chew can include *cannabis* material comprising coarsely cut fan leaf material, and an additive solution comprising grain alcohol, a *cannabis* extract oil, and honey, wherein the *cannabis* material has an average particle size of greater than 2 mm. The coarsely cut *cannabis* material can be in the form of elongated strips.

Figure 2:
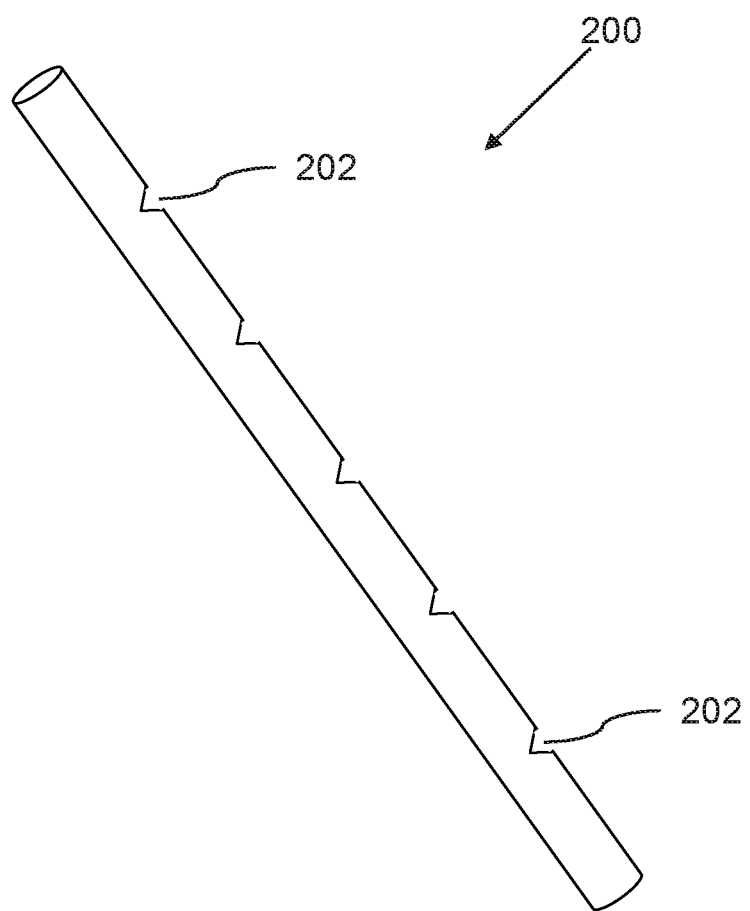
FIG. 2 is a perspective of a scored *cannabis* stick, according to an embodiment of the invention.

In a related embodiment, a *cannabis* composition, configured as a stick, can include a *cannabis* material comprising finely cut sugar leaf material, and an additive solution comprising grain alcohol, a *cannabis* extract oil, and honey, wherein the *cannabis* composition can be compressed into a solid and stable shape, such as a compressed sheet, a bar, or a stick 200, such as shown in FIG. 2. In certain embodiments, the stick or bar can be scored, with scores 202 or notches 202, such that a user can easily break off parts of the stick or bar, similar to a scored chocolate bar.

In a related embodiment, wherein the *cannabis* composition is configured as a compressed sheet, bar, or stick, more honey can be added to improve the binding capability of the *cannabis* composition when compressed, such that the *cannabis* composition can comprise about 10 ml of honey per ounce of *cannabis* material, or a range of 5 to 20 ml of honey per ounce of *cannabis* material.

In a related embodiment, a *cannabis* composition for medical use can include *cannabis* extract oil, such that single-dosage formulation of the *cannabis* composition includes 10 mg of THC.

In a related embodiment, a *cannabis* composition can be packaged in a 7 gram single-dosage formulation for out-of-state patients or other users.

In a related embodiment, as shown in FIG. 1, a method of manufacture of a *cannabis* composition adapted for oral use 100, can include:
  a) providing a *cannabis* material 102;
  b) adding an additive solution to the *cannabis* material 104, thereby creating a *cannabis* composition;
  c) allowing the *cannabis* composition to ferment for a first period of time 106;
  d) heating the *cannabis* material at a first temperature for a second period of time 108.

In a related embodiment, fermentation can be aided by fungi and/or microorganisms present in the *cannabis* material, by addition of a yeast, such as brewer's yeast to the additive solution, and/or by use of *cannabis* material grown with fertilizer comprising brewer's yeast.

In a related embodiment, as shown in FIG. 1, the step 102 of providing *cannabis* material can include flower material, sugar leaf material, fan leaf material, or a combination thereof, harvested from *cannabis* plants. The *cannabis* material can be washed, such as in lukewarm water, in order to remove debris from the material, after which the *cannabis* material can be allowed to dry or cure to the desired dryness.

In a related embodiment, the *cannabis* material can be processed by separating the flowers, sugar leaves, and/or fan leaves. In certain embodiments, the *cannabis* material can be weighed after separation in order to obtain an accurate accounting of the material being used.

In a related embodiment, the *cannabis* material can be ground, shredded, sifted, or otherwise broken up into finely cut *cannabis* material and/or coarsely cut *cannabis* material, either by hand or by machine. In certain embodiments, the *cannabis* material is ground after it is separated into flowers, sugar leaves, and/or fan leaves. In other embodiments, the flowers, sugar leaves, and/or fan leaves can be ground together.

In a related embodiment, the *cannabis* material can be disinfected or sterilized. Disinfection can be performed using any suitable method, including using an antimicrobial agent, applying grain alcohol, ultra-violet radiation, or heat to the *cannabis* material. Disinfection can include eliminating, inactivating or killing a substantial percentage of harmful organisms, such as bacteria, mold, or mold spores, from the *cannabis* material or completely sterilizing the *cannabis* material.

In a related embodiment, as shown in FIG. 1, the step 104 of adding a solution can include combining an additive solution with the *cannabis* material, wherein the additive solution can comprise grain alcohol, honey, a *cannabis* extract, or a combination thereof, as previously described. The addition of the alcohol solution and the flavoring agent to the *cannabis* material can create a *cannabis* composition.

In a related embodiment, as shown in FIG. 1, the step 106 of fermenting can include allowing the *cannabis* composition to ferment for a first period of time. The first period of time can be in a range of approximately 6 to 36 hours, 6 to 12 hours, 12 to 20 hours, 18 to 30, 24 to 49 hours, or some other predetermined period of time. In certain embodiments, the first period of time can be in the range of approximately 20 to 28 hours. Fermentation of the *cannabis* material can cause the amount of carbohydrates and polyphenols in the *cannabis* material to decrease, thereby changing the taste and texture of the *cannabis* material.

In a related embodiment, as shown in FIG. 1, following the end of the first period of time of fermentation, the step 108 can include heating the *cannabis* composition at a first temperature for a second period of time. Heating the *cannabis* composition starts a process known as decarboxylation, wherein the naturally occurring, non-psychoactive cannabinoid tetrahydrocannabinolic acid (THCA) is chemically converted to its psychoactive form, THC. Decarboxylation in *cannabis* generally starts at approximately 150° F. and continues to approximately 250-300° F., where lower temperatures require longer to complete decarboxylation than higher temperatures.

In a related embodiment, decarboxylation can be used as a final method of disinfecting or sterilizing the *cannabis* composition, as the heating process can kill remaining harmful organisms in or on the *cannabis* composition, and can terminate the fermentation process.

In a related embodiment, the first temperature can be in the range of approximately 150° F. to 300° F., 180° F. to 270° F., 200° F. to 250° F., or 220° F. to 235° F. In certain embodiments, the first temperature can be in a range of approximately 150° F. to 250° F.

In a related embodiment, the second period of time can be in a range of approximately 15 to 90 minutes. In certain embodiments, typically when making a chew or a dip, the second period of time can be 30 minutes, or in a range of approximately 15 to 45 minutes. In other embodiments, typically when making a compressed stick or brick, the second period of time can be approximately an hour, or in a range of approximately 45 to 75 minutes.

In a related embodiment, heating the *cannabis* composition can include gradually raising the temperature of the *cannabis* composition from the first temperature to a second temperature during the second period of time. The first temperature can be in the range of approximately 100° F. to 150° F. and the second temperature can be in the range of approximately 150° F. to 300° F. In certain embodiments, the first temperature can be in the range of approximately 110° F. to 140° F. and the second temperature can be in the range of approximately 150° F. to 250° F.

In a related embodiment, heating the *cannabis* composition can include exposing the composition to heat in an oven or similar apparatus. In certain embodiments, the *cannabis* composition can be heated using microwave radiation. For example, the *cannabis* material can be heated in a 1000 W microwave for approximately 1-5 minutes.

Here has thus been described a multitude of embodiments of both a smokeless *cannabis* composition and a process for producing smokeless *cannabis*, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A *cannabis* composition adapted for oral use, comprising:
    a) a *cannabis* material; and
    b) an additive solution, comprising honey and a *cannabis* extract;
    wherein the *cannabis* extract is a *cannabis* extract oil comprising a concentration of tetrahydrocannabinol in a range of 15 to 70 percent by volume of the *cannabis* extract oil;
    wherein the *cannabis* extract oil is in a range of 0.25 gram to 1 gram per ounce of the *cannabis* material, and the honey is in a range of 2.5 to 10 ml per ounce of the *cannabis* material.

2. The *cannabis* composition of claim 1, wherein the additive solution further comprises rectified alcohol with a concentration in a range of 90 to 98 percent alcohol by volume.

3. The *cannabis* composition of claim 1, wherein the *cannabis* composition is configured as a dip, such that the *cannabis* material has an average particle size in a range of 0.3 mm to 2 mm, wherein the *cannabis* material comprises flower material from a *cannabis* plant.

4. The *cannabis* composition of claim 3, wherein the *cannabis* material is the flower material from the *cannabis* plant.

5. The *cannabis* composition of claim 1, wherein the *cannabis* composition is configured as a chew, such that the *cannabis* material has an average particle size greater than 2 mm, wherein the *cannabis* material comprises a fan leaf material from a *cannabis* plant.

6. The *cannabis* composition of claim 5, wherein the *cannabis* material is the fan leaf material from the *cannabis* plant.

7. The *cannabis* composition of claim 1, wherein the *cannabis* composition is configured as a stick, wherein the *cannabis* material comprises a sugar leaf material from a *cannabis* plant, wherein the *cannabis* composition is compressed to a stick shape, and wherein the honey is in a range of 2.5 to 10 ml per ounce of the *cannabis* material.

8. The *cannabis* composition of claim 7, wherein the *cannabis* material is the sugar leaf material from the *cannabis* plant.

9. The *cannabis* composition of claim 1, wherein the *cannabis* material comprises at least 70% of the total dry weight of the *cannabis* composition.

10. The *cannabis* composition of claim 1, wherein the *cannabis* material is made from a *cannabis* plant that has been grown using a fertilizer comprising *Saccharomyces cerevisiae*.

11. The *cannabis* composition of claim 1, wherein the additive solution further comprises *Saccharomyces cerevisiae*.

12. A method of manufacture of a *cannabis* composition adapted for oral use, comprising:
    a) providing a *cannabis* material;
    b) adding an additive solution to the *cannabis* material, wherein the additive solution comprises honey and a *cannabis* extract, thereby creating a *cannabis* composition;
    c) allowing the *cannabis* composition to ferment for a first period of time; and
    d) heating the *cannabis* material to a predetermined temperature for a second period of time;
        wherein the *cannabis* extract is a *cannabis* extract oil comprising a concentration of tetrahydrocannabinol in a range of 15 to 70 percent by volume of the *cannabis* extract oil;
        wherein the *cannabis* extract oil is in a range of 0.25 gram to 1 gram per ounce of the *cannabis* material, and the honey is in a range of 2.5 to 10 ml per ounce of the *cannabis* material.

13. The method of claim 12, wherein the additive solution further comprises rectified alcohol with a concentration in a range of 90 to 98 percent alcohol by volume.

14. The method of claim 12, wherein the *cannabis* material has an average particle size in a range of 0.3 mm to 2 mm, wherein the *cannabis* material comprises flower material from a *cannabis* plant, such that the *cannabis* composition is configured as a dip.

15. The method of claim 12, wherein the *cannabis* material has an average particle size greater than 2 mm, wherein the *cannabis* material comprises a fan leaf material from a *cannabis* plant, such that the *cannabis* composition is configured as a chew.

16. The method of claim 12, wherein the *cannabis* material comprises sugar leaf material from a *cannabis* plant, the method further comprising compressing the *cannabis* composition into a compressed stick shape, such that the *cannabis* composition is configured as a stick, wherein the honey is in a range of 2.5 to 10 ml per ounce of the *cannabis* material.

17. The method of claim 12, wherein the first period of time is in a range of 12 to 36 hours.

18. The method of claim 12, wherein the predetermined temperature is in a range of 150° F. to 250° F.

19. The method of claim 12, wherein the second period of time is in a range of 15 to 45 minutes.

20. The method of claim 16, wherein the second period of time is in a range of 45 to 75 minutes.

21. The method of claim 12, wherein the *cannabis* material is made from a *cannabis* plant that has been grown using a fertilizer comprising Saccharomyces cerevisiae.

22. The method of claim 12, wherein the additive solution further comprises Saccharomyces cerevisiae.

23. A *cannabis* composition adapted for oral use, comprising:
   a) a *cannabis* material; and
   b) an additive solution, comprising honey, Saccharomyces cerevisiae, and a *cannabis* extract.

24. The *cannabis* composition of claim 23, wherein the *cannabis* extract is a *cannabis* extract oil comprising a concentration of tetrahydrocannabinol in a range of 15 to 70 percent by volume of the *cannabis* extract oil.

25. The *cannabis* composition of claim 24, wherein the *cannabis* extract oil is in a range of 0.25 gram to 1 gram per ounce of the *cannabis* material, and the honey is in a range of 2.5 to 10 ml per ounce of the *cannabis* material.

26. The *cannabis* composition of claim 23, wherein the additive solution further comprises rectified alcohol with a concentration in a range of 90 to 98 percent alcohol by volume.

27. The *cannabis* composition of claim 23, wherein the *cannabis* composition is configured as a dip, such that the *cannabis* material has an average particle size in a range of 0.3 mm to 2 mm, wherein the *cannabis* material comprises flower material from a *cannabis* plant.

28. The *cannabis* composition of claim 1, wherein the *cannabis* composition is configured as a chew, such that the *cannabis* material has an average particle size greater than 2 mm, wherein the *cannabis* material comprises a fan leaf material from a *cannabis* plant.

29. The *cannabis* composition of claim 1, wherein the *cannabis* composition is configured as a stick, wherein the *cannabis* material comprises a sugar leaf material from a *cannabis* plant, wherein the *cannabis* composition is compressed to a stick shape, and wherein the honey is in a range of 2.5 to 10 ml per ounce of the *cannabis* material.

30. The *cannabis* composition of claim 1, wherein the *cannabis* material comprises at least 70% of the total dry weight of the *cannabis* composition.

* * * * *